(12) United States Patent
Pauser et al.

(10) Patent No.: US 7,922,486 B2
(45) Date of Patent: Apr. 12, 2011

(54) CAPSULE FOR STORAGE, MIXING AND DISPENSING MATERIALS

(75) Inventors: Helmut Pauser, Diessen (DE);
Sebastian Guggenmos, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/514,400

(22) Filed: Aug. 31, 2006

(65) Prior Publication Data

US 2007/0048688 A1    Mar. 1, 2007

(30) Foreign Application Priority Data

Sep. 1, 2005   (EP) .................... 05019024

(51) Int. Cl.
*A61C 5/04*    (2006.01)
*A61M 37/00*   (2006.01)

(52) U.S. Cl. ................. 433/89; 433/80; 604/82

(58) Field of Classification Search ............. 433/80–90; 206/219; 604/82, 89; 222/41, 44, 47, 49
See application file for complete search history.

(56) References Cited

U.S. PATENT DOCUMENTS

| | | | |
|---|---|---|---|
| 4,449,645 A | 5/1984 | Korwin et al. | 222/49 |
| 4,674,661 A | 6/1987 | Herold | 222/386 |
| 5,509,530 A * | 4/1996 | Wilson | 206/220 |
| 5,743,431 A | 4/1998 | Brattesani | 222/1 |
| 6,698,446 B2 * | 3/2004 | Cornwell | 137/115.16 |
| 7,306,390 B2 * | 12/2007 | Quintero et al. | 401/133 |
| 2003/0176834 A1 * | 9/2003 | Horth et al. | 604/85 |
| 2004/0020796 A1 | 2/2004 | Cheetham et al. | 206/63.5 |
| 2006/0118107 A1 * | 6/2006 | King | 128/200.23 |

FOREIGN PATENT DOCUMENTS

EP       0 783 872     7/1997

* cited by examiner

*Primary Examiner* — Cris L Rodriguez
*Assistant Examiner* — Yogesh Patel

(57) ABSTRACT

A capsule for storage, mixing, and dispensing of dental material, including an indicator for indicating proper activation of the capsule. The indicator may indicate that a minimum required displacement of an applicator member or of an activator member, or both, has occurred.

46 Claims, 5 Drawing Sheets

CAPSULE FOR STORAGE, MIXING AND DISPENSING MATERIALS

CROSS REFERENCE TO RELATED APPLICATIONS

This application claims priority to European Patent Application No. 05019024.8, filed Sep. 1, 2005.

FIELD OF THE INVENTION

The present invention relates to a capsule for storage, mixing and dispensing of materials, preferably dental materials, most preferably glass ionomer cements. In particular, the present invention relates to a capsule for storage, mixing and dispensing materials which preferably consist of a plurality of, i.e., two or more components.

BACKGROUND OF THE INVENTION

Mixing capsules which are filled with the components in separate chambers by the manufacturer are used to produce mixtures of two or more components. The components are brought into communication and mixed with one another by the user, for example by destroying a wall separating the chambers.

Mixing capsules for the production of dental materials which are often mixed from a pulverulent component and a liquid component, the mixing procedure usually taking place in a shaker unit, are known in the dental sector. The completely mixed substance is then dispensed directly onto the working area, for example into a tooth cavity, through a dispensing spout formed integrally on the mixing capsule.

SUMMARY OF THE INVENTION

The object of the invention is to provide a capsule for storage, mixing and dispensing of materials that reduces the risk of use of the capsule if dispensing of a precise mixture is not guaranteed. This object is achieved with the features of the claims.

According to a first aspect, the invention provides a capsule for storage, mixing, and dispensing of dental material comprising an indicator for indicating proper activation of the capsule. Thus, once the capsule has been activated either manually by the user or automatically when the capsule is placed in a shaker unit for mixing the components, the activation state, i.e. properly activated, only partly activated, or still inactivated, can be readily seen by the user before the mixture is applied to the working area.

According to the present invention, the term "properly activated" means that the components in the capsule that are to be mixed have been essentially completely brought in contact with each other. The term "partly activated" means that at least one component has not been completely brought in contact with the other component or components. The term "inactivated" means that the components to be mixed are separated from each other.

According to a preferred embodiment of the invention, the capsule comprises a capsule body member providing a main chamber and a dispensing opening, an applicator member being slidably accommodated in the capsule body member, and an activator member that is slidably accommodated in the applicator member. The activator member and the applicator member form an auxiliary chamber.

The indicator of the capsule preferably indicates that a minimum required displacement of the applicator member and/or the activator member has occurred. In particular, the indicator indicates proper positioning of the capsule body member, the applicator member, and the activator member relative to each other. If the indicator indicates proper activation of the capsule, for example if the capsule is removed from the shaker unit, the user knows that the components contained in the capsule have been completely brought into contact with each other, which is a critical pre-condition to the components contained in the chambers may properly mixed. The capsule is thus in a state that allows dispensing of the mixture onto the working area.

Capsules of the type of the present invention are typically placed in a shaker unit where they are shaken for a certain period of time for mixing of the components. Activation (i.e., bringing the components together), and mixing happens during this procedure. Thus, the capsule of the present invention is "self-activating". In more detail, the inactivated capsule is placed in the shaker unit. In the shaker unit, the components within the capsule are mixed by a reciprocating movement of the shaker unit. After starting this reciprocating movement, the capsule is automatically activated due to the forces acting on the capsule along its longitudinal axis during shaking, the activator member and the applicator member are automatically moved into the capsule body member, and the size of the capsule is reduced. At some point, a trough-hole in the applicator member reaches a bypass recess, and the components are brought in contact with each other.

Preferably, the indicator is formed by a first aperture provided in the capsule body member, and a second aperture provided in the applicator member. The second aperture is provided such that it is aligned or overlaps with the first aperture upon proper activation of the capsule. More preferably, the capsule comprises further a marker provided at the activator member. The marker is provided such that it is aligned or overlaps with the first and second apertures upon proper activation of the capsule. Thus, if the two apertures overlap, and if the marker can be seen through the aligned apertures, the user can see via the indicator that the capsule is internally properly activated.

The marker preferably is an optical marker. Alternatively, the marker is a structural marker. In case of an optical marker, the marker is preferably a colored area, more preferably a colored area which color is different from the color of the capsule body member. Alternatively, the colored area is colored different from the applicator and the capsule body member. As a further alternative, the marker provides a pattern in form of a roughened surface, in contrast to a generally smooth surface of the activator member (or the other way round). In case of a structural marker, the marker may be a raised area. The raised area may, for example, snap into the aperture of the applicator member so that it can be seen through the aligned apertures. Moreover, the user may recognize this by an audible click when the marker snaps into the aperture(s).

The first aperture preferably extends through the capsule body member wall, for example, perpendicular to the longitudinal axis of the capsule. It is preferred that the first aperture is located in the proximity of the back end of the capsule body member. The second aperture preferably extends through the applicator member wall, also for example perpendicular to the longitudinal axis of the capsule. Preferably, the second aperture is located in the proximity of the back end of the applicator member. The first and the second aperture preferably extend in the same radial direction relative to the longitudinal axis of the capsule.

The capsule of the first aspect of the present invention preferably has a variable length, wherein a reduced length of the capsule provides an indicator indicating proper activation of the capsule. Capsules of the invention are typically used in combination with an applier, into which the capsule is placed for dispensing of the mixed material. Thus, if the length of the capsule is not sufficiently reduced, it does not fit into the applier which indicates improper activation of the capsule. On the other hand, if the capsule is properly activated, the variable length is reduced to such an extent that the capsule fits into the applier. This indicates proper activation of the capsule, whereas activation may be done manually or automatically within the shaker unit.

According to a second aspect, the invention provides a capsule for storage, mixing, and dispensing of dental material having variable length, wherein a reduced length of the capsule provides an indicator indicating proper activation of the capsule. The capsule of the second aspect of the invention preferably comprises a capsule body member providing a main chamber and a dispensing opening, an applicator member that is slidably accommodated in the capsule body member; and an activator member that is slidably accommodated in the applicator member. The activator member and the applicator member form an auxiliary chamber.

The indicator indicates that a minimum required displacement of the applicator member and/or the activator member has occurred. Preferably, the indicator indicates proper positioning of the capsule body member, the applicator member, and the activator member relative to each other. If the capsule is not activated properly, the activator member and the applicator member project from the capsule body member too far, and therefore the capsule cannot be placed into the applier for dispensing of the mixture.

According to a third aspect, the invention provides a capsule for storage, mixing, and dispensing of dental material comprising a capsule body member providing a main chamber and a dispensing opening, and an applicator member being slideably accommodated in the capsule body member. The applicator member provides an auxiliary chamber. An open ring is provided between the capsule body member and the applicator member. The open ring of the capsule preferably is a cylindrical ring.

The cylindrical ring preferably comprises a slit through the ring wall and extends parallel to the longitudinal axis of the ring. The open ring is preferably made from a material providing low friction such as fluoropolymers, polyolefins or plastics with "lubricant fillers", such as unsaturated fatty monoamides. Preferably, there is little press fit between the capsule body member, the open ring, and the applicator member.

Preferably, the capsules according to the first and the second aspect also comprise such a sealing ring.

Preferably, the capsule further comprises an activator member that is slideably accommodated in the applicator member.

Furthermore, the capsule of the second aspect preferably comprises an indicator for indicating proper activation of the capsule by the user. The indicator indicates minimum required displacement of the applicator member and/or the activator member. More preferably, the indicator indicates proper positioning of the capsule body member, the applicator member, and the activator member relative to each other. As described above, the indicator of the capsule of the third aspect of the present invention is preferably formed by a first aperture provided in the capsule body member, and a second aperture provided in the applicator member. The second aperture is provided such that it is aligned or overlaps with the first aperture upon proper activation of the capsule.

The open ring preferably comprises a third aperture being provided such that it is aligned or overlaps with the first aperture and that it is aligned or overlaps with the second aperture upon proper activation of the capsule.

The capsule further preferably comprises a marker provided at the activator member. The marker is provided such that it is aligned or overlaps with the first, second and third apertures upon proper activation of the capsule.

In the following, preferred features of all three aspects of the present invention are described.

The inner wall of the capsule body member preferably comprises a recessed area. Furthermore, the applicator member comprises a through-hole extending from the auxiliary chamber to the outer circumferential surface of the applicator member. It is preferred that the open ring sealingly covers the through-hole in the applicator member. The through-hole and the recessed area form a channel between the auxiliary chamber and the main chamber upon activation of the capsule (e.g. by the user pushing the activator member). The main chamber and the auxiliary chamber are selectively connectable for fluid communication between the chambers upon activation of the capsule, wherein movement of the activator member towards the dispensing opening causes movement of the applicator member so that the channel between the auxiliary chamber and the main chamber is opened.

The radially extending through-hole in the applicator member is initially covered by the wall of the capsule body member. Alternatively, the radially extending through-hole is initially covered by the wall of the open ring. The ring is preferably made from a material that provides low friction. Furthermore, the slit in the ring allows the ring to deform to some extent to conform precisely to the surface of the applicator member. A light, press fit between the capsule body member, the ring, and the applicator member provides good sealing while the low friction material still allows displacement of the applicator member in the shaker unit. This is advantageous because the activating forces of the shaker unit are typically small, for example 15 to 20 N.

The radially extending through-hole is preferably located in close proximity to the separation wall of the applicator member separating the auxiliary chamber from the mixing chamber. Preferably, the through-hole extends essentially perpendicularly to the longitudinal axis of the applicator member. Alternatively, the through-hole extends essentially at an angle smaller than 90° to the longitudinal axis of the applicator member, whereas the through-hole is inclined to the capsule's front side.

According to a preferred embodiment, the separation wall comprises a raised area extending towards the activator member. Preferably, the raised area comprises an annular bulge. Once the activator member contacts the raised area of the applicator member, all liquid contained in the auxiliary chamber has been channeled into the main chamber, i.e. the mixing chamber.

Preferably, the capsule comprises a dispensing cannula connected to the dispensing opening. The dispensing cannula is preferably integrally formed with the capsule body member. For example, the dispensing cannula is connected with the capsule body member via two-shot injection molding. Preferably, the cannula is rotatably connected to the capsule body member thus providing a valve.

According to the invention it is preferred that the capsule is dimensioned such that it is receivable by an applier only in a state of proper activation.

The dental materials are preferably glass ionomer cements or resin modified glass ionomer cements. The main chamber may contain a first, preferably powdery, component of the material, and the auxiliary chamber may contain a second, preferably liquid, component of the material.

The activator member is moveable along a longitudinal axis within the applicator member, and the applicator member is moveable within the capsule body member so as to displace a liquid contained in the auxiliary chamber from the auxiliary chamber into the main chamber. In a first step, the activator member is moved so that the liquid contained in the auxiliary chamber is mixed with the substance contained in the main chamber. Upon mixing of these components, the mixture is dispensed through the dispensing opening by a movement of the activator member and the applicator member.

Upon application of a force on the activator member, both the activator member and the applicator member move into the capsule body member due to, e.g., hydraulic transmission. The displacement of the liquid contained in the auxiliary chamber takes place as soon as the radially extending through-hole of the applicator member reaches the recessed area of the capsule body member while moving the two members into the capsule body member. As an advantage of this design, a complete emptying of the receptacle during mixing is facilitated, thus providing a higher reliability of the mixing ratio.

According to the invention, all parts within the capsule, i.e. the applicator member and the activator member move smoothly, i.e. are displaceable smoothly. This provides the possibility to activate the capsule only by means of the force that is applied the mixing process. There is no manual activation required, i.e. the capsule according to the present invention is a self-activating capsule. It can just be placed in the mixing device which shakes the capsule along its longitudinal axis. This reciprocating motion self-activates the capsule because the applied forces push the activator towards the applicator until flow communication between the main chamber and the auxiliary chamber is established. The components are then brought into contact and mixed with each other. This results in a simplified handling and also essential time savings to the dentist.

In order to achieve smooth movement of the parts the sealing members and/or the surfaces facing the seals are optionally coated with a lubricant, e.g. silicon oil. As an option, the lubricant is preferably included in the material of the seal and/or the other parts, e.g. as an additive (such as unsaturated fatty monoamides).

According to a fourth aspect, the invention provides a kit, comprising at least one of the capsules of any of the first or second aspect of the present invention in combination with an applicator into which the capsule fits.

According to a fifth aspect, the invention provides the use of the capsules of the first, second, or third aspect for mixing a material of two or more components.

The capsule according to the invention is advantageous because correct activation of the capsule is visible for the dentist which reduces the risk for failures.

BRIEF DESCRIPTION OF THE DRAWINGS

The invention will be described in more detail in the following with reference to the drawings in which.

DETAILED DESCRIPTION OF THE PREFERRED EMBODIMENTS

Figure 1:
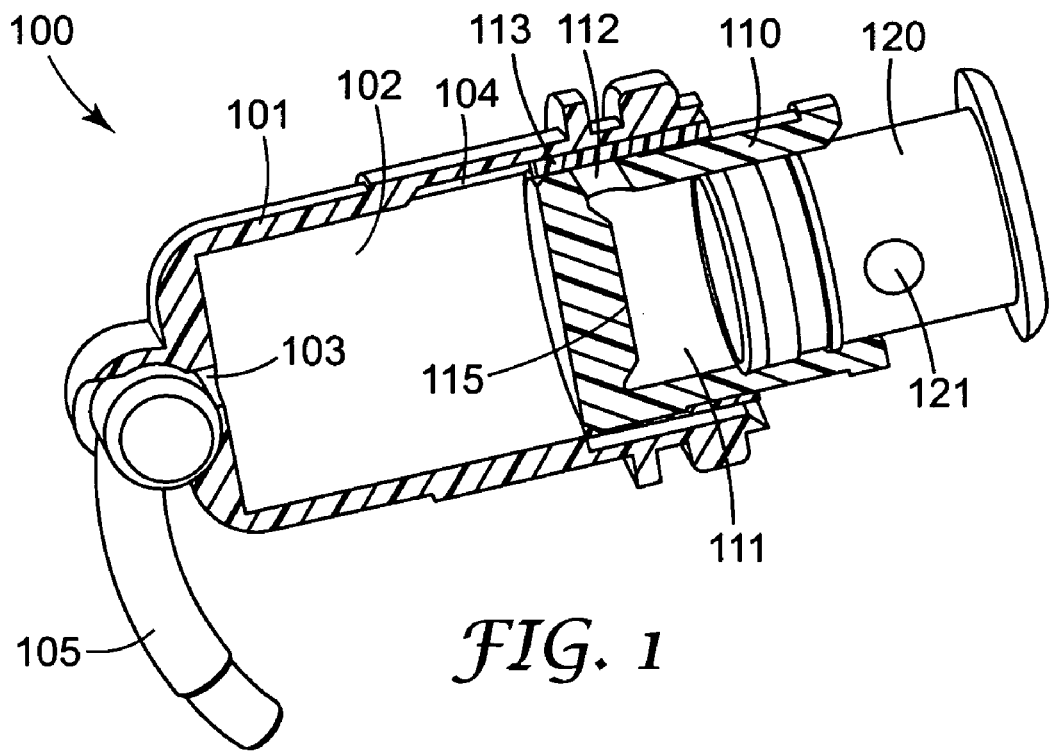
FIG. 1 shows a cross-sectional view of an inactivated capsule of the invention.

FIG. 1 shows a capsule 100 for storage, mixing and dispensing of materials according to a first aspect of the present invention. The capsule 100 comprises a capsule body member 101 that contains a main chamber 102, i.e. a mixing chamber. Furthermore, the capsule body member 101 comprises a dispensing opening 103. In the embodiment shown in FIG. 1, a pivotable dispensing or discharge cannula 105 is connected to the dispensing opening 103. The pivotable cannula 105 acts as a valve. Preferably, the dispensing cannula is connected with the capsule body member via two-shot injection molding. As shown in FIG. 1, the capsule body member 101 is open at one end (in the figure at the right side) in order to receive an applicator member or piston 110. The applicator member or piston 110 is slideably moveable in the capsule body member 101. Movement of the piston towards a direction of the cannula 105 reduces the volume of the mixing chamber 102. The applicator piston 110 in turn accommodates an activator member or stamp 120 so that an auxiliary chamber 111 is formed by the applicator member 110 and the activator member 120. FIG. 1 also shows a marker 121 at the outer surface of the activator member 120.

The applicator piston 110 comprises a through-hole 112 that extends radially from the auxiliary chamber 111 to the outer surface of the applicator 110. As shown in FIG. 1, before activation of the capsule, the radially extending through-hole 112 is covered or closed by the wall of the capsule body member 101. In order to obtain a channel for fluid communication between the main chamber 102 and the auxiliary chamber 111, the capsule body member 101 comprises a recessed area 104, i.e. a bypass. Upon activation of the capsule, the applicator piston 110 is moved towards the dispensing opening 103. At some point, the through-hole 112 in the applicator piston 110 reaches the bypass 104. At that point, the main chamber 102 and the auxiliary chamber 111 are connected with each other via the bypass 104 and the through-hole 112.

The through-hole 112 is preferably covered by a sealing ring 113 at the outer surface of the applicator piston 110, i.e. sealing ring 113 covers the radially outer opening of through-hole 112. In the non-activated position of the applicator piston 110 shown in FIG. 1, the inner surface of the capsule body member 101 supports the sealing ring 113. However, upon activation of the applicator piston 110, the applicator piston 110 is displaced relative to the sealing ring 113, and the through-hole 112 is then facing the recessed area 104. The material contained in the auxiliary chamber 111 can flow into the mixing chamber 102. The sealing ring 113 will be described in more detail below.

As shown in FIG. 1, the separation wall between the auxiliary chamber and the main chamber preferably comprises a raised area 115, like a bulge.

Figure 2:
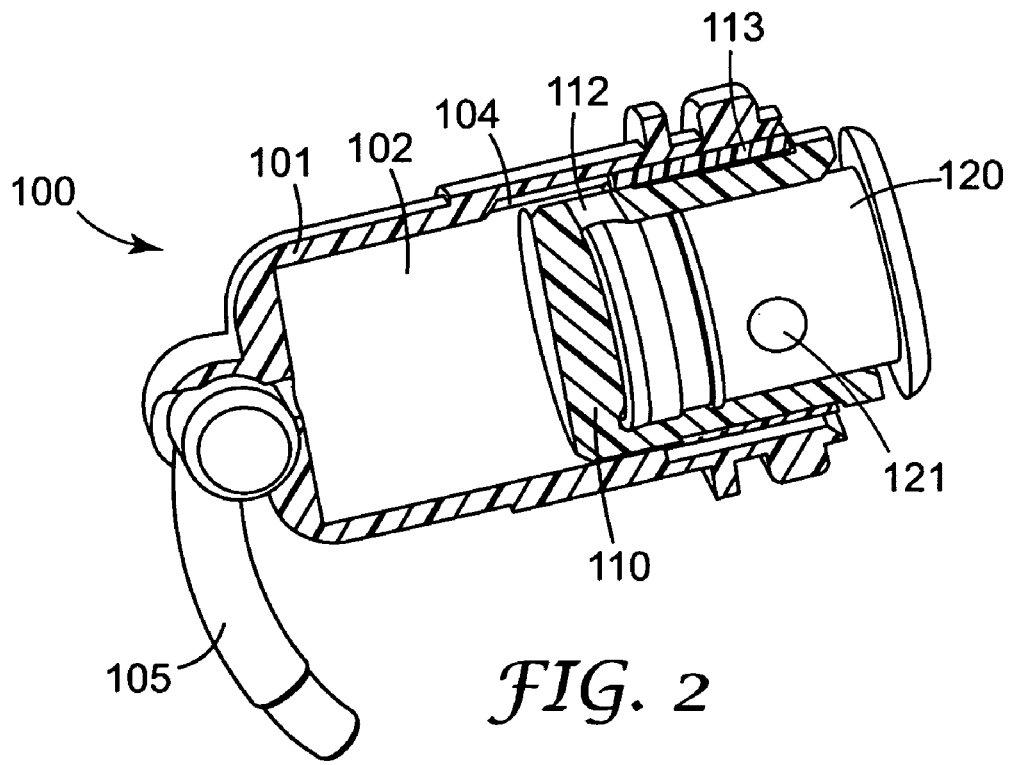
FIG. 2 shows the capsule of FIG. 1 in its activated state.

The fully activated capsule according to the invention is shown in FIG. 2. The activator member 120 is fully received in the applicator member 110 so that the material contained in the auxiliary chamber is pushed through the through-hole 112 and the bypass 104 into the main chamber 102. This properly activated state is usually achieved during shaking of the capsule 100 in a shaker unit for mixing the components in the main chamber 102. After shaking, when the activator member 120 together with the applicator member 110 is further moved into the capsule body member 101, the mixed material will be dispensed through the cannula 105.

The front end surface of the activator stamp 120 facing the auxiliary chamber 111 is preferably flat. However, dependent on the liquids to be used, the front end preferably comprises non-flat shapes, for example a reverse truncated shape, i.e., with a central recess (see, for example, FIG. 3). This ensures that the activator stamp 120 first contacts the outer area of the surface of the material contained in the auxiliary chamber 111.

Figure 3:
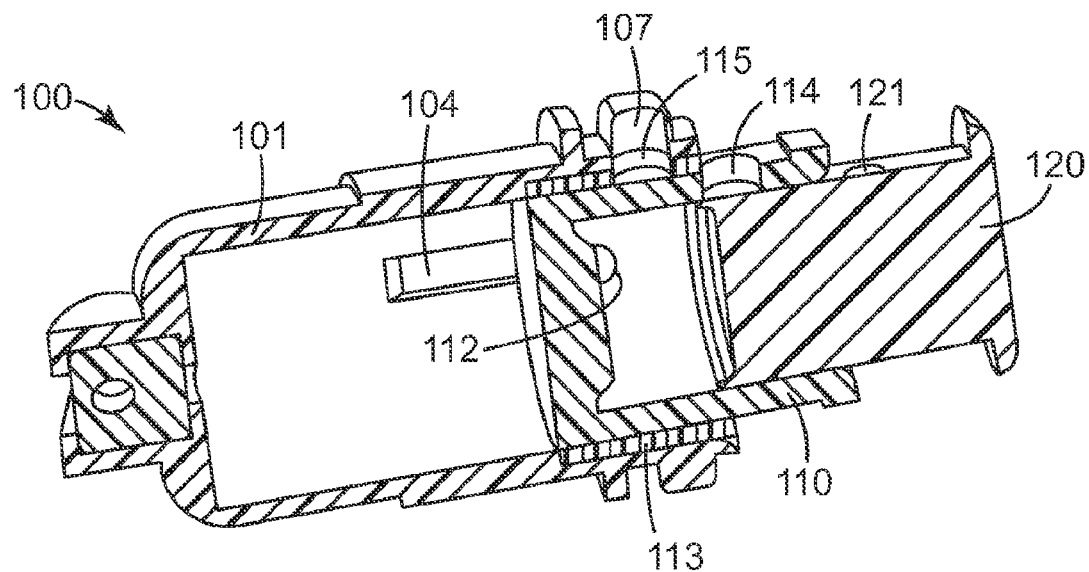
FIG. 3 shows a different cross-sectional view of the capsule of FIG. 1.

FIG. 3 shows the details of the first aspect of the present invention. FIG. 3 is also a cross-sectional view of the capsule of FIG. 1 but the view is 90° shifted with respect to the section of FIG. 1.

The capsule body member 101 of capsule 100 comprises an aperture 107 that extends radially from the interior of the capsule body member 101 to the outside of the capsule 100. In the embodiment shown in FIG. 3, the aperture 107 extends perpendicular to the longitudinal axis of the capsule 100. The aperture 107 is located at the back end of the capsule body member 101.

Figure 4:
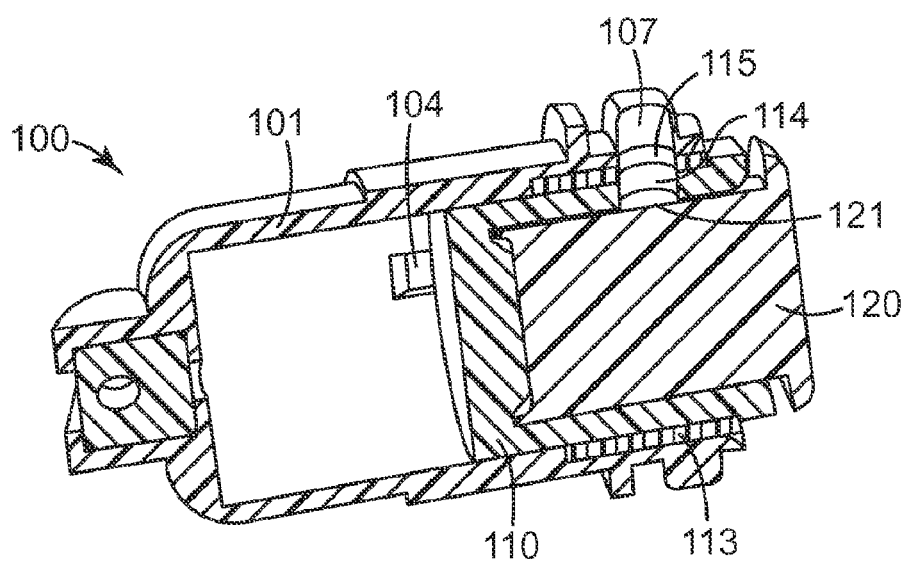
FIG. 4 shows a different cross-sectional view of the capsule of FIG. 2.

The applicator member 110 also comprises an aperture 114. As shown in FIG. 3, the aperture 114 extends from the interior of the applicator member 110 to the outer surface of the applicator member 110, preferably perpendicular to the axis of the capsule 100. The aperture 114 of the applicator member 110 is located at the back end of the applicator member, and such that the two apertures overlap or are aligned when the capsule is properly activated, as shown in FIG. 4. The apertures need not necessarily be located at the back end of the capsule body member 101 or the applicator member 110 as long as they are aligned with each other in a relative position of the applicator member 110 to the capsule body member 101 in which the capsule is properly activated.

The activator member 120 preferably comprises a marker 121 on its outer surface. The marker 121 is located at a position such that the marker 121 is aligned with the two apertures 107, 114 when the activator member 120 is fully received in the applicator member 110, i.e., when the capsule is properly activated for mixing. This state is shown in FIG. 4.

The marker is preferably a color marker that is visible by the user through the apertures 107, 114 once the capsule is activated. The fact that the marker is visible through the apertures 107, 114 indicates the user that the capsule 100 is fully, i.e., properly activated. As an alternative to a color marker, the surface of the activator member 120 may be roughened at this spot (assuming that the remaining surface of the activator member 120 is smooth—or the other way round). The roughened pattern would then be visible by the user through the apertures 107, 114. As a further alternative, the marker is a physical marker like a small protrusion that snaps into the aperture(s).

In case the capsule 100 also comprises the sealing ring 113 according to the third aspect of the present invention, the sealing ring 113 also comprises an aperture 115. A shown in FIG. 3, the aperture 115 of the sealing ring 113 already overlaps with the aperture of the capsule body member 101.

Figure 5:
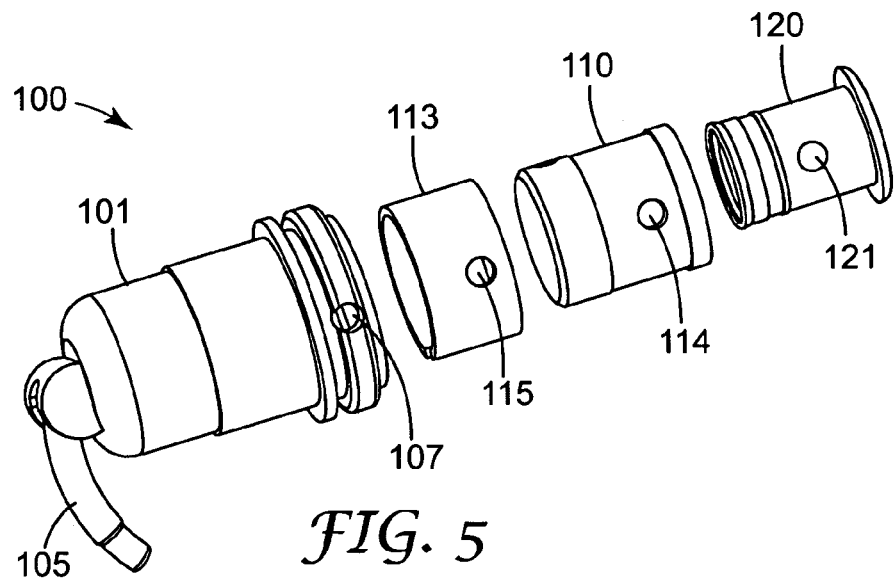
FIG. 5 shows an exploded perspective view of the capsule of FIG. 1.

In the exploded view of FIG. 5, the capsule body member 101, sealing ring 113, applicator member 110, and activator member 120 are shown. The three apertures 107, 114, and 115 as well as the marker 121 are also shown.

Figure 6:
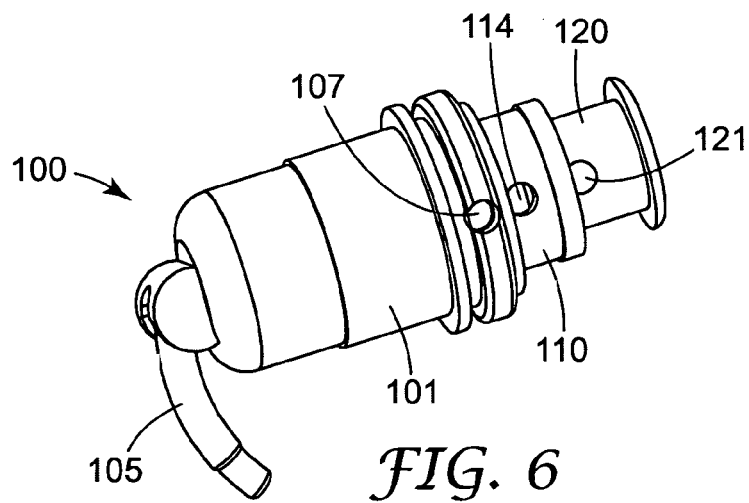
FIG. 6 shows a perspective view of the capsule of FIG. 1.

FIG. 6 shows a perspective of the assembled capsule 100 in its original, i.e., inactivated state. The aperture 114 of the applicator member 110 is not aligned with the aperture 107 of the capsule body member 101. Through the aperture 107, the color of the applicator member 110 is visible. Moreover, the activator member 120 is still visible through the aperture 114 of the applicator member 110.

Figure 7:
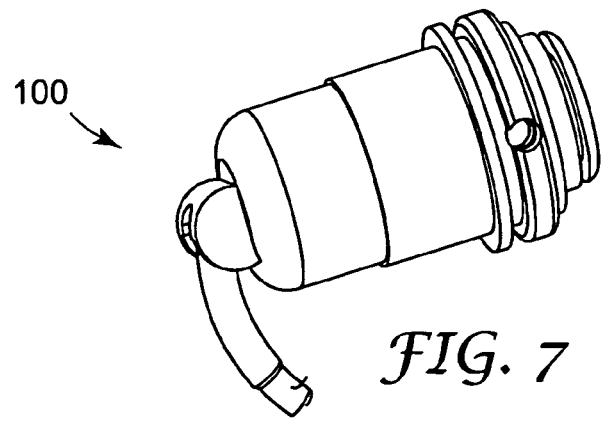
FIG. 7 shows a perspective view of the capsule of FIG. 2.

Proper activation is indicated to the user in FIG. 7. Here, the color of the marker 121 which is different from the color of the remainder of the surface of the activator member 120 is visible through the aligned apertures. In this state, the capsule 100 can be placed into an applier 200 (see FIG. 9), and the mixed material can be dispensed (see FIG. 10).

Figure 8:
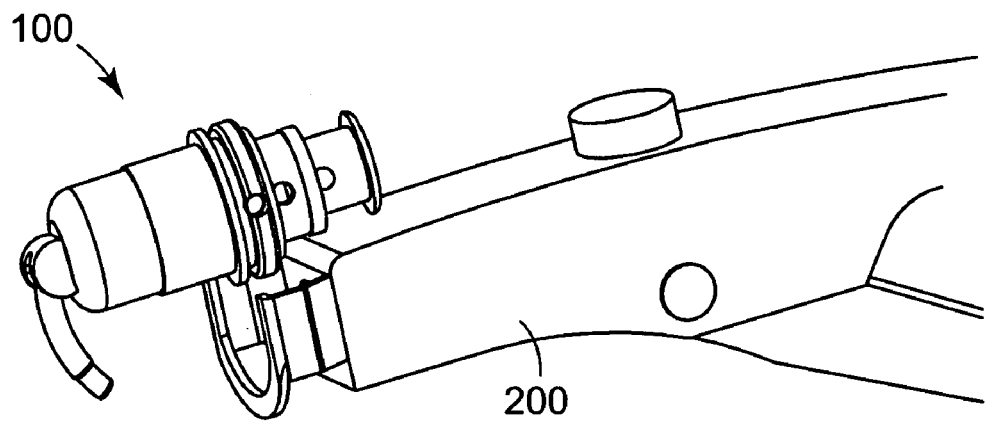
FIG. 8 shows the inactivated capsule of FIG. 1 in combination with an applier.
Figure 9:
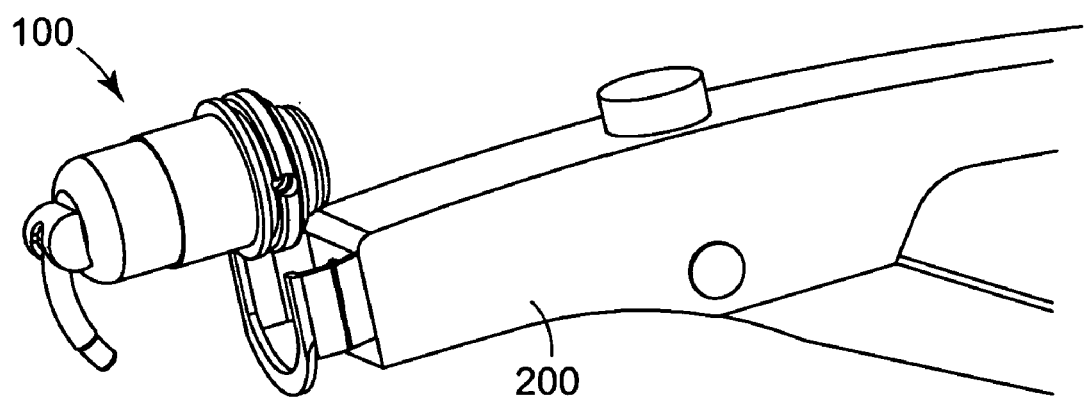
FIG. 9 shows a properly activated capsule as shown in FIG. 2 in combination with an applier.
Figure 10:
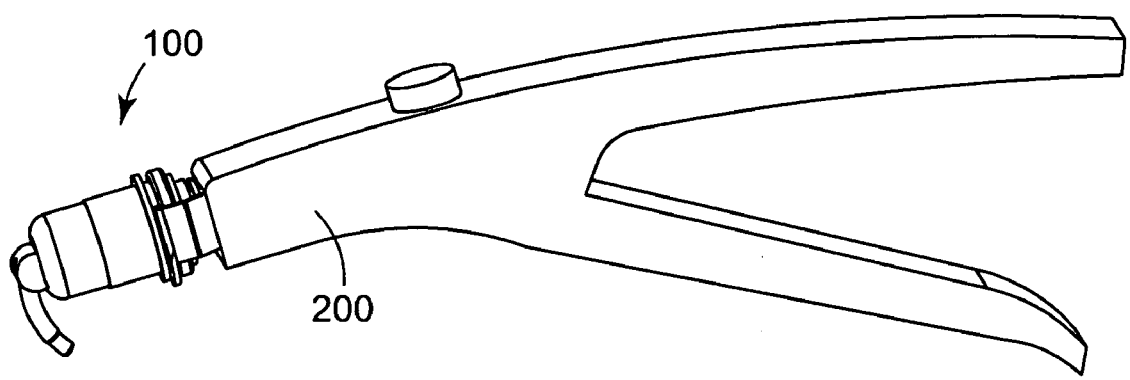
FIG. 10 shows the properly activated capsule according to the present invention being placed into the applier.

According to a second aspect, the present invention provides a capsule for storage, mixing, and dispensing of dental material having variable length, wherein a reduced length of the capsule provides an indicator indicating proper activation of the capsule. This is also shown in FIGS. 8 and 9. FIG. 8 shows an inactivated capsule 100 and the front end of the applier 200. It can be seen that the capsule cannot be placed into the applier because its length has not been sufficiently reduced. In FIG. 9 the capsule 100 is shown in a state allowing the capsule to be placed into the applier 200. It can be clearly seen that there is no state between the two shown in FIGS. 8 and 9 allowing the capsule 100 to be placed into the applier, which ensures that only properly activated capsules can be used with the applier.

The invention claimed is:

1. Capsule for storage, mixing, and dispensing of dental material comprising:
   a capsule body member providing a main chamber and a dispensing opening;
   an applicator member slidably accommodated in the capsule body member;
   an activator member slidably accommodated in the applicator member, the activator member and the applicator member forming an auxiliary chamber; and
   an indicator for providing a visual indication to a user of the proper activation of the capsule, the indicator comprising a first aperture provided in the capsule body member, a second aperture provided in the applicator member, and a marker provided at the activator member, such that the marker is aligned with the first and second apertures upon proper activation of the capsule.

2. The capsule of claim 1, wherein the marker is an optical marker.

3. The capsule of claim 2, wherein the optical marker is a colored area.

4. The capsule of claim 3, wherein the colored area is a different color from the capsule body member.

5. The capsule of claim 3, wherein the colored area is colored differently from the applicator and the capsule body member.

6. The capsule of claim 1, wherein the marker is a structural marker.

7. The capsule of claim 6, wherein the structural marker is a raised area.

8. The capsule of claim 1, wherein the first aperture extends through the capsule body member wall.

9. The capsule of claim 8, wherein the first aperture extends perpendicular to the longitudinal axis of the capsule.

10. The capsule of claim 8, wherein the first aperture is located in the proximity of the back end of the capsule body member.

11. The capsule of claim 1, wherein the second aperture extends through the applicator member wall.

12. The capsule of claim 11, wherein the second aperture extends perpendicular to the longitudinal axis of the capsule.

13. The capsule of claim 12, wherein the first and the second aperture extend in the same radial direction relative to the longitudinal axis of the capsule.

14. The capsule of claim 11, wherein the second aperture is located in the proximity of the back end of the applicator member.

15. The capsule of claim 1, the capsule having a variable length, wherein a reduced length of the capsule provides an indicator indicating proper activation of the capsule.

16. The capsule of claim 1, wherein the indicator indicates that a minimum required displacement of the applicator member and/or the activator member has occurred.

17. The capsule of claim 16, wherein the indicator indicates proper positioning of the capsule body member, the applicator member, and the activator member relative to each other.

18. The capsule of claim 1, further comprising a dispensing cannula connected to the dispensing opening.

19. The capsule of claim 18, wherein the dispensing cannula is integrally formed with the capsule body member.

20. The capsule of claim 18, wherein the dispensing cannula is connected with the capsule body member via two-shot injection molding.

21. The capsule of claim 18, wherein the cannula is rotatably connected to the capsule body member thus providing a valve.

22. The capsule of claim 1, being dimensioned such that it is receivable by an applier only in a state of proper activation.

23. The capsule of claim 1, wherein the dental materials are glass ionomer cements or resin modified glass ionomer cements.

24. The capsule of claim 1, wherein the main chamber contains a first, powdery component of the material, and the auxiliary chamber contains a second, liquid component of the material.

25. Kit, comprising at least one capsule according to claim 1 and an applicator into which the capsule fits.

26. The capsule of claim 1, wherein the indicator indicates proper positioning of the capsule body member, the applicator member, and the activator member relative to each other.

27. Capsule for storage, mixing, and dispensing of dental material comprising: a capsule body member providing a main chamber and a dispensing opening; an applicator member being slideably accommodated in the capsule body member, the applicator member providing an auxiliary chamber; and a sealing ring provided between the capsule body member and the applicator member, the sealing ring having an aperture adapted for alignment with an aperture in the capsule body member and with a marker provided at an activator member to provide an indicator for providing a visual indication to a user indicating proper activation of the capsule, wherein the capsule body member is adapted to slidably accommodate an activator member.

28. The capsule of claim 27, further comprising an activator member being slideably accommodated in the applicator member.

29. The capsule of claim 27, wherein the sealing ring is a cylindrical ring.

30. The capsule of claim 29, wherein the cylindrical ring comprises a slit through the ring wall and extending along the longitudinal axis of the ring.

31. The capsule of claim 27, wherein the indicator indicates minimum required displacement of the applicator member and/or the activator member.

32. The capsule of claim 31, wherein the indicator indicates proper positioning of the capsule body member, the applicator member, and the activator member relative to each other.

33. The capsule of claim 27, wherein the sealing ring is made from a material providing low friction.

34. The capsule of claim 27, wherein there is little press fit between the capsule body member, the sealing ring, and the applicator member.

35. The capsule of claim 27, wherein the inner wall of the capsule body member comprises a recessed area.

36. The capsule of claim 27, wherein the applicator member comprises a through-hole extending from the auxiliary chamber to the outer circumferential surface of the applicator member.

37. The capsule of claim 36, wherein the sealing ring covers and seals the through hole in the applicator member.

38. The capsule of claim 36, wherein the through-hole and the recessed area forming a channel between the main chamber and the auxiliary chamber upon activation of the capsule by the activator member.

39. The capsule of claim 36, wherein the through-hole in the applicator member is initially covered by the wall of the capsule body member.

40. The capsule of claim 36, wherein the through-hole in the applicator member is initially covered by the wall of the sealing ring.

41. The capsule of claim 36, wherein the through-hole is located in close proximity to a wall of the applicator member separating the auxiliary chamber from the mixing chamber.

42. The capsule of claim 41, wherein the wall comprises a raised area extending towards the activator member.

43. The capsule of claim 42, wherein the raised area comprises an annular bulge.

44. The capsule of claim 36, wherein the through-hole extends essentially perpendicularly to the longitudinal axis of the applicator member.

45. The capsule of claim 36, wherein the through-hole extends essentially at an angle smaller than 90° to the longitudinal axis of the applicator member.

46. The capsule of claim 27, the main chamber and the auxiliary chamber being selectively connectable for fluid communication between the chambers upon activation of the capsule by the activator member, wherein movement of the activator member towards the dispensing opening causes movement of the applicator member so that the channel between the main chamber and the auxiliary chamber is opened.

* * * * *

UNITED STATES PATENT AND TRADEMARK OFFICE
CERTIFICATE OF CORRECTION

| | | |
|---|---|---|
| PATENT NO. | : 7,922,486 B2 | Page 1 of 1 |
| APPLICATION NO. | : 11/514400 | |
| DATED | : April 12, 2011 | |
| INVENTOR(S) | : Helmut Pauser | |

It is certified that error appears in the above-identified patent and that said Letters Patent is hereby corrected as shown below:

Column 5

Line 27; After "applied" insert -- by the holding clamp of the mixing device, i.e., the shaker unit, at the very beginning of --.

Signed and Sealed this
Third Day of July, 2012

David J. Kappos
*Director of the United States Patent and Trademark Office*